(12) United States Patent
Green

(10) Patent No.: US 6,552,063 B2
(45) Date of Patent: Apr. 22, 2003

(54) PHENYLBUTAZONE CARRIER FORMULATION

(76) Inventor: George Green, 1030 W. Commodore Blvd., Jackson, NJ (US) 08527

( * ) Notice: Subject to any disclaimer, the term of this patent is extended or adjusted under 35 U.S.C. 154(b) by 3 days.

(21) Appl. No.: 09/920,875

(22) Filed: Aug. 3, 2001

(65) Prior Publication Data

US 2002/0025978 A1 Feb. 28, 2002

Related U.S. Application Data

(60) Provisional application No. 60/227,266, filed on Aug. 24, 2000.

(51) Int. Cl.⁷ ............................................. A61K 31/415
(52) U.S. Cl. ........................ 514/404; 514/407; 424/489; 424/493; 424/442
(58) Field of Search ................................. 514/404, 407; 424/489, 493, 442

(56) References Cited

U.S. PATENT DOCUMENTS 6,022,563 A * 2/2000 Gordon ...................... 424/489

* cited by examiner

Primary Examiner—Rebecca Cook
(74) Attorney, Agent, or Firm—Clifford G. Frayne

(57) ABSTRACT

A formulation for delivery of phenylbutazone for the treatment of equine ailments is disbursed homogeneately in a powdered carrier agent having a flavoring agent and a coloring agent in an amount of from 5 to 49.9 percent by weight of the formulation.

7 Claims, No Drawings

PHENYLBUTAZONE CARRIER FORMULATION

RELATED APPLICATIONS

Applicant claims the benefit of provisional application 60/227,266, filed Aug. 24, 2000.

BACKGROUND OF THE INVENTION

1. Field of the Invention

The invention relates to non-steroidal anti-inflammatory drugs, and in particular, to a new and improved carrier formulation for delivery of phenylbutazone and equivalents thereof which is particularly palatable to horses and methods of preparing same.

2. Description of the Prior Art

Phenylbutazone is a useful, non-steroidal, anti-inflammatory veterinary pharmaceutical which has gained wide acceptance. It is the preferred choice for the treatment of equine modalities when an illness or injury necessitates the use of a pain killer or anti-inflammatory medication. Phenylbutazone is used to treat joint deterioration, swelling, and inflammation from injuries, as well as skeletal muscular disorders and various other pains experienced by horses.

The drug has been used to treat horses for more than 30 years and despite this long term acceptance of use, there still persists many problems in administering the drug. Phenylbutazone is most often administered orally and its bitter taste oftentimes causes the horse to reject the drug which can result in inconsistent dosages and extreme difficulty in administering the drug to the horse. Phenylbutazone typically was available to horse owners and veterinarians in one gram tablets for oral administration. Horses will not willingly eat the tablets and normally the owner or veterinarian requires the aid of a groom in order to restrain the horse and take effective measures to orally administer the tablet.

Attempts at granulation of phenylbutazone and the mixing with feed has been attempted, however, in this method, inconsistent dosages are oftentimes realized.

While the administration of phenylbutazone in these forms is an inconvenience to horse owners and veterinarians, it is necessary for the health of the horse. In order to control or relieve inflammation and pain, a proper and effective dosage of phenylbutazone must be administered to the horse, repeatedly, over a particular time frame. In addition, the phenylbutazone which is administered should be in the form that can undergo rapid intestinal absorption. Veterinarians will typically prescribe a dosage to be administered three times a day since it takes approximately 3 to 5 hours for phenylbutazone to achieve an effective blood concentration level. However, due to the problems with oral administration of tablets and similar forms, horse owners and even veterinarians may settle for a single administration a day, but double or triple the dosage which defeats the efficacy of phenylbutazone.

Applicant has overcome these problems by developing a formulation in which phenylbutazone in powdered form is mixed with a powdered carrier base and at least one flavoring agent which formulation is adhereable to a horse's feed and which is palatable to horses. As such, the horse owner and veterinarian can be assured that the effective and full dosage of the medication as prescribed is being administered and ultimately absorbed by the horse.

OBJECTS OF THE INVENTION

An object of the present invention is to provide for a novel formulation for the administration of phenylbutazone.

Another object of the present invention is to provide for a novel formulation for the administration of phenylbutazone, the formulation being palatable to the horse.

A still further object of the present invention is to provide for a novel formulation for the administration of phenylbutazone which does not interfere or delay the intestinal absorption of phenylbutazone and is palatable, therefore readily and completely consumed.

SUMMARY OF THE INVENTION

A food additive formulation for the administration of phenylbutazone comprising a powdered carrier blended with the phenylbutazone and a flavoring agent to mask the taste of phenylbutazone, the formulation being in the range of 5% to 49.9% by weight phenylbutazone, but preferably 10% by weight, the formulation blended and treated as such that the powdered formulation is adhereable to the food of the animal.

DETAILED DESCRIPTION

Applicant's formulation comprises phenylbutazone, a carrier agent, a flavoring agent, and a coloring or dye agent. Phenylbutazone is present in the range of from 5 to 49.9% by weight. The carrier agent is present from 49.98% to 94.88% by weight. The flavoring agent is present at about 0.10% by weight and the coloring agent is present at about 0.02% by weight.

The preferred carrier agent is dextrose and the preferred flavoring agent is an orange flavor. The color agent is FDC Yellow No. 6. The preferred blend of ingredients is phenylbutazone present at 10% by weight, dextrose present at 89.88% by weight and the orange flavor and FDC Yellow No. 6 present at the original weight percentages.

The method of preparation calls for the flavoring agent, in this instance, orange flavor, and the coloring agent FDC Yellow No. 6 to be premixed with 10% of the total amount of the dextrose. Separately, half of the total weight percent of the dextrose and half of the total weight percent of the phenylbutazone is mixed in a twin shell blender. The premix of the orange flavor, FDC Yellow No. 6 and 10% of the dextrose is then added and mixed. The remaining half of the phenylbutazone and the remaining portion of dextrose is then added to the blender in that order and mixed for one hour. The dextrose and orange flavoring agent coat the phenylbutazone granules, thus masking the taste of the phenylbutazone. The carrier agent, preferably dextrose, has a natural tackiness such that it adheres to the food, particularly cellulosic food to which it is added, therefore insuring that the animal gets the full correct dosage.

The advantage of the product is that it is taste acceptable (pallatable) by the horse being treated, and therefore is complete consumed. In a 24 hour double-blind cross over study, this product proved to be the bioequivalent to the pioneer product.

In two palatability studies carried out in 115 horses, the drug was consumed by over 80% of the animals within 30 minutes, which meets the FDA/CVM requirements.

It will be recognized by those or ordinary skill in the art that certain changes and additions can be made to the aforesaid formulation without departing from the spirit and scope of the invention. It is therefore manifestly intended that the invention be limited only by the claims and the equivalents thereof.

I claim:

1. A formulation for the delivery of phenylbutazone comprising:

a powdered carrier agent; and a therapeutically effective amount of phenylbutazone for the treatment of equine ailments selected from the group consisting of joint deterioration, swelling and inflammation, said phenylbutazone being dispersed to homogeneity in said powdered carrier in an amount ranging from 5 to 49.9 percent by weight of the formulation; and a flavoring agent and a coloring agent.

2. The carrier formulation as set forth in claim 1 wherein said powdered carrier agent is dextrose.

3. The carrier formulation as set forth in claim 1 wherein said powdered carrier agent is lactose.

4. The carrier formulation in accordance with claim 1 wherein said flavoring agent is an orange flavoring agent.

5. The carrier formulation as set forth in claim wherein said coloring agent is FDC Yellow No. 6.

6. The carrier formulation as set forth in claim 1 wherein said phenylbutazone is present in an amount of 10 percent by weight, said powdered carrier agent is present in 88.88 percent by weight, said flavoring agent is present in approximately 0.10 percent by weight, and said coloring agent is present in approximately 0.02 percent by weight.

7. A method for the treatment of an equine ailment in a horse selected from the group consisting of joint deterioration, swelling and inflammation comprising administering to said horse a formulation comprising phenylbutazone a powdered carrier, flavoring agent and coloring agent, wherein said phenylbutazone is disbursed to homogeneity in said powdered carrier in an amount ranging from 5 to 49.9 percent by weight.

* * * * *